United States Patent [19]

Macors et al.

[11] Patent Number: 5,282,822

[45] Date of Patent: Feb. 1, 1994

[54] LANCET EJECTOR FOR LANCET INJECTOR

[75] Inventors: Paul P. M. G. J. Macors, Liege, Belgium; Gregory G. Acker, Springboro, Pa.

[73] Assignee: Sherwood Medical Company, St. Louis, Mo.

[21] Appl. No.: 4,885

[22] Filed: Jan. 19, 1993

[51] Int. Cl.$^5$ .............................................. A61B 17/32
[52] U.S. Cl. ............................ 606/182; 606/167; 606/181; 606/185; 604/187; 604/232; 604/235
[58] Field of Search ............... 604/134, 135, 136, 157, 604/187, 220, 232, 235; 606/167, 172, 181, 182, 185, 188, 189

[56] References Cited

U.S. PATENT DOCUMENTS

| | | | |
|---|---|---|---|
| 3,744,493 | 6/1973 | Booher et al. | 604/235 |
| 4,379,456 | 4/1983 | Cornell et al. | 606/182 |
| 4,469,110 | 9/1984 | Slama . | |
| 4,484,910 | 11/1984 | Sarnoff et al. | 604/134 |
| 4,503,856 | 3/1985 | Cornell et al. | 606/182 |
| 4,517,978 | 5/1985 | Levin et al. . | |
| 4,580,565 | 4/1986 | Cornell et al. | 606/182 |
| 4,653,513 | 3/1987 | Dombrowski . | |
| 4,658,821 | 4/1987 | Chiodo et al. . | |
| 4,841,985 | 6/1989 | Wanamaker . | |
| 4,895,147 | 1/1990 | Bodicky et al. | 606/182 |
| 4,974,603 | 12/1990 | Jacobs . | |
| 4,976,724 | 12/1990 | Nieto et al. | 606/181 |
| 4,984,580 | 1/1991 | Wanamaker . | |

*Primary Examiner*—C. Fred Rosenbaum
*Assistant Examiner*—Noelle Kent Gring
*Attorney, Agent, or Firm*—Andrew J. Beck; Montgomery W. Smith; Curtis D. Kinghorn

[57] ABSTRACT

A lancet injector is provided having a lancet tip that may be automatically removed from the lancet injector after piercing and being retracted from the skin of the subject. A separation recess extends from the slot along the housing toward the proximal end of the housing allowing the control member to move proximally into the separation recess. The separation recess has a proximally extending retention recess that retains the lancet holder in its most proximal position. The lancet holder has a bore extending longitudinally through it aligned with the central axis of the housing. A pin extends from the proximal end of the housing along the central axis of the housing toward the central bore of the holder. The control member moves into the separation recess causing the pin to enter the bore of the lancet holder and contact the lancet. The pin stops proximal movement of the lancet during further proximal movement of the control member in the separation recess thereby causing the lancet to be pushed to the edge of frictional contact with the lancet holder. Movement of the control member proximally into the retention recess moves the lancet out of frictional contact with the holder. Thereafter, the distal end of the housing is directed downward causing the lancet to fall into an appropriate sharps container.

31 Claims, 7 Drawing Sheets

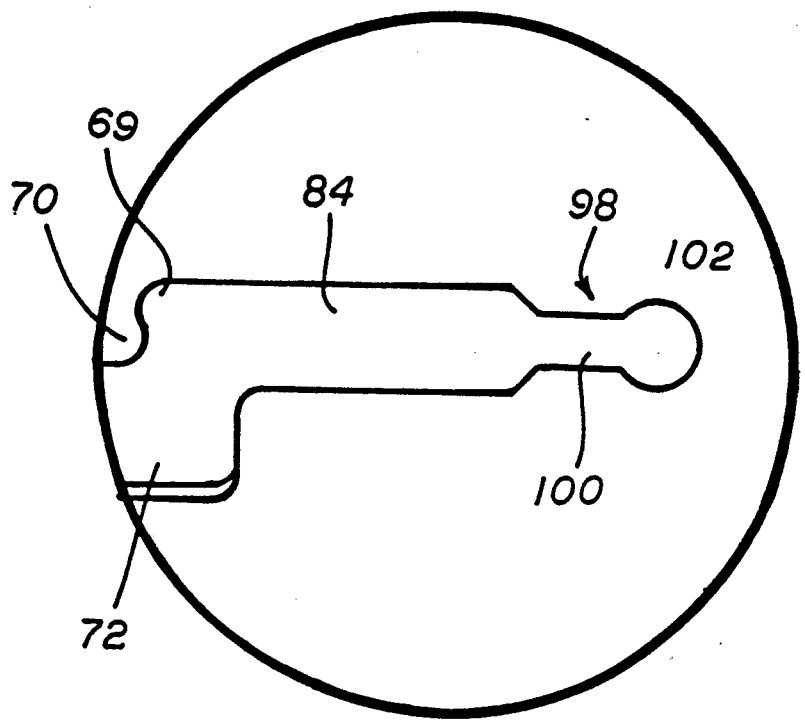
FIG. 13
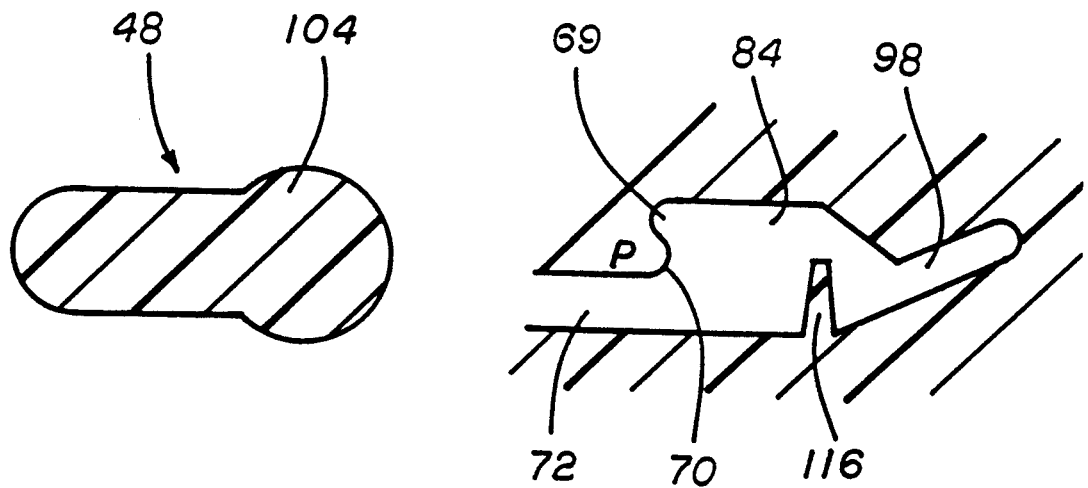
FIG. 14
FIG. 18

LANCET EJECTOR FOR LANCET INJECTOR

BACKGROUND OF THE INVENTION

1. Field of the Invention

The invention relates to lancet injectors and more particularly to lancet injectors having lancet tips that are automatically removable from the lancet injector without requiring hand contact with the lancet.

2. Description of Related Art

Lancets are used to pierce the skin of a subject, usually through the finger. Blood then flows through the incision where it can be collected for testing in a blood collection tube such as a capillary tube or pipette.

Historically, early lancets generally had a handle and a needle extending therefrom. However, numerous problems are inherent with such lancets such as controlling the depth and angle of penetration by the needle, controlling the force of the insertion, and the psychological affect to the user of seeing the exposed needle.

One attempt to avoid these and other problems with this early type of lancet was to create lancets having needles that are spring loaded to be injected into and removed from the subject's skin. Typically, these devices hide the needle both before and after the incision is made to prevent its view by the subject and to prevent inadvertent contact with the needle. An example of such a lancet injector is disclosed in U.S. Pat. No. 4,580,565 issued on Apr. 8, 1986 to W. D. Cornell and C. Evans and its parent application U.S. Pat. No. 4,503,856, issued to W. D. Cornell and C. Evans on Mar. 12, 1985, both assigned to the assignee of the present application.

The invention disclosed herein is an improvement of the lancet injector described in these two patents. Consequently, in order to better understand the present invention, a verbatim detailed description and FIGS. 1–6 of the lancet injector of the two above-referenced patents are set out herein in their entirety:

"Referring now to the drawings and particularly to FIGS. 1 and 2, a lancet injector 10 is shown including an elongate, generally cylindrical, housing 12 having a chamber or bore 14, and a lancet holder 16 slidable in the housing bore 14. Housing 12 has a proximal end 18 in which is secured an end plug 20, and a distal end 22 covered by a removable cap 24 having a central opening 25. Cap 24 is frictionally held in place by an annular bead 26 on the exterior of housing 12. In this way, the cap 24 can be snapped on and off the distal end 22 of the housing.

The lancet holder 16, as also seen in FIG. 3, includes a generally cylindrical portion or slide 28 having a lancet holding member 30 integrally connected to the distal end of the slide and a cylindrical extension or spring connector 32 at the proximal end of the slide. A spring 34, shown as a coil spring, is disposed in the bore 14 between the holder 16 and the plug 20. Spring 34 is shown engaged between the holder and a lower end portion of the housing. The connector 32 is provided with a series of external integral bumps 36 disposed in a spiral arrangement for threadedly receiving and holding the upper or distal end of coil spring 34. The spring 34 is threaded onto connector 32 until the end of the spring engages an integral stop bump 38. The end plug 20 is shown provided with an integral extension or spring connector 40 having a spiral series of integral bumps 42 which threadedly receives and, as shown, holds the lower end of coil spring 34. The spring 34 is threaded onto connector 40 until the end of the spring engages an integral stop bump 44. If desired, the spring connectors 32 and 40 may be provided with suitable screw threads instead of the series of bumps or the ends of the spring 34 may be fixed to those connectors by other suitable means.

The slide 28 has a hole 46 in which is secured a manual slide control member or control latch 48 which extends through a slot, indicated generally at 50, in the sidewall of the housing 12. Latch 48 extends to the exterior of the housing so that it provides an exterior manual control movable along the slot 50 for positioning the lancet holder 16 in a number of positions, as will be further described.

In assembling the device 10, the opposite ends of spring 34 may be respectively threaded onto connectors 32 and 40 to provide unitary assembly, as seen in FIG. 3. This assembly can be inserted into the proximal end of the housing 12. The free length of the spring 34 is such that the unit may be manually rotated in the housing 12 by rotating plug 20 until the hole 46 appears in the slot 50. The latch 48 may then be inserted through the slot and into hole 46. The latch 48 is fixed in the hole 46, for example, it may be adhesively connected or solvent bonded to the sidewalls of hole 46.

The holder 16 and connected latch 48 are preferably spring biased in a counterclockwise direction of rotation, as viewed in the drawings, that is arcuately toward engagement with the left sidewall 52 of slot 50. This may be accomplished by providing the plug 20 and inner wall of the housing 12 at its proximal end with cooperating surfaces which permit insertion of the plug in a selected relative position with respect to slide 28. For example, as shown in FIG. 3, the plug 20 is provided with a plurality of flats 54 which register with a plurality of flats 56 (FIG. 2) on the inner sidewall of bore 14 at the proximal end 18. In this way, after the latch 48 is secured in hole 46, the plug 20 can be rotated counterclockwise so that the latch 48 engages a wall of slot 50, and then the plug 20 is further rotated in the same direction a slight amount relative to holder 16, and then the plug is inserted into the end 18 of the housing. Because of the cooperating flats 54 and 56, the plug cannot rotate and remains in its inserted position with the spring 34 resiliently biasing the holder 16 and latch 48 leftwardly or counterclockwise toward the left edge 52 of slot 50. The plug 20 may be adhesively connected such as by applying a suitable adhesive to the plug prior to insertion or a suitable solvent where the plug and housing materials can be solvent bonded.

The lancet holding member 30 is shown as a sleeve or cylindrical barrel having inner sidewalls 58 which frictionally engage outer peripheral surfaces of a lancet 60. The lancet 60 is shown including a base or handle 62, such as of plastic material, and a needle 64, such as a solid stainless steel pointed needle. The handle 62 may be molded about the needle so that the tip of the needle extends outwardly beyond the upper end 66 of the handle. In FIG. 4, the lancet 60 is shown including an integrally molded needle cap or sheath 68 covering the pointed needle tip. The connection between the sheath 68 and the handle 62 is fragile so that by twisting or rotating the sheath relative to the handle, and then pulling the sheath from the needle tip, the needle tip is exposed. The depth of the lancet holding member 30 is less than the length of the lancet handle 62 so that the upper portion, such as its upper one half, extends out of the holder and may be grasped, for example, between the thumb and finger, for inserting the lancet 60 into the holder 30 and for removing it after use. The bottom of the lancet bottoms on the bottom of the member 30 as shown in FIG. 2.

The slot 50, as best seen in FIGS. 1, 2 and 5, is shaped so as to have a relative wide portion at the proximal end of the slot through which the control member 48 can be moved. In FIGS. 1 and 2, the member 48 is shown in its retracted position which places holder 16, member 30, and lancet 60 in the retracted position with the needle tip wholly within the housing 12. The control member 48 is shown releasably latched in an axial recess 69 having a downward protrusion 70 for securely holding the lancet holder in the retracted position. When the lancet holder 30 is in the retracted position, the spring 34 is in compression and exerting maximum longitudinal or linear spring force on the holder 16 in the distal direction. Also, the holder 16 is held in recess 69 against the biasing force of spring 34.

When the control member 48 is manually unlatched from the retracted position (FIGS. 1 and 2), such as by moving it leftward over the protrusion 70 by applying pressure with a finger or thumb, the holder 16, due to the force of spring 34 and inertia, moves swiftly linearly or longitudinally and distally through housing bore 14 to a skin piercing position wherein the point of needle 64 extends through opening 25 in the end cap 24 and distally of the distal end of the housing as shown in phantom in FIG. 5. During this movement control member 48 moves along a slot portion 72. The holder 16 and lancet 60 are quickly linearly retracted to a neutral position, that is, with the point of needle 64 retracted or withdrawn from the incision and within the housing 12 as shown in FIG. 5. Spring 34 is sized relative to housing 12 such that when the holder 16 and control member 48 are in this neutral position, the spring 34 is at its free length position or neutral force position, that is, spring 34 is substantially neither in tension nor compression.

In moving from the retracted position of FIG. 1 to the skin penetrating position shown in phantom in FIG. 5, it is primarily the inertia or momentum of the moving holder 16 that causes the lancet to move distally past the neutral position of the holder or free length position of the distal end of spring 34 (position shown in full in FIG. 5). Since the distal end of spring is extended distally beyond the position it would have when the spring 34 in its neutral or free length condition due primarily to the inertia of the moving holder 16, the spring is tensioned and therefore swiftly retracts or moves the needle point proximally from the piercing position back to the neutral position.

The parts may be proportioned such that the extent of distal travel of the lancet 60 may be limited by the engagement of the control member 48 with a sidewall 74 (FIGS. 1, 5 and 6) of the slot 50, the indicated phantom position of member 48 in FIG. 5, or, if desired, by the engagement of the upper end 66 of the lancet handle with the inner side of the end wall of cap 24. In some cases, the construction may allow the end 66 to strike the skin.

The holder 16 and lancet holder 30 may be moved to a lancet access or unloading and loading position, the position shown in FIG. 6. This is accomplished by removing cap 24 and urging the control member 48 rightwardly against the bias force from its neutral position of FIG. 5 and into an elongate slot portion 76 of slot 50, then longitudinally or linearly upwardly and distally into an enlarged slot portion 78, and then leftwardly into the access position in a recess 80 in slot 50 and which has a distally extending sidewall 82 holding the member 48 in place. During this distal movement in slot portion 76 the coil spring 34 is tensioned, that is, stretched beyond its neutral or free length condition of FIG. 5. The tensioned spring 34 tends to maintain the member 48 urged downwardly in groove 80 so that it cannot move out of the groove.

In the lancet access condition of holder 16, as shown in FIG. 6, the lancet holding member 30 extends through and above the upper or distal open end of the housing 12. In this position the upper portion of the lancet 60 may be grasped by the handle 62 and pulled upwardly to remove it from the member 30. A new lancet may then be inserted into the holder 30 until it bottoms against the inner bottom wall of the member 30. After a new lancet is inserted into the holding member in the access position of FIG. 6, the needle sheath such as sheath 68 (FIG. 4) is removed to expose the pointed needle tip, and then the external control member 48 is manually moved out of recess 80 into the enlarged slot portion 78. The member 48 is moved rightwardly against the rotary bias force of spring 34 into an elongate slot 76 where the force of tensioned spring 34 swiftly moves the slide 28 proximally longitudinally or axially of the housing so that it moves back into its neutral position shown in FIG. 5, the bias force of the spring urging it against the left edge 52 of the slot 50. The cap 24 may then be snapped back onto the distal end of housing 12.

In use, a new lancet, such as lancet 60, is inserted into the lancet holder 30 when the control member 48 is positioned in the lancet access position indicated in FIG. 6. The needle sheath, such as sheath 68 (FIG. 4) is removed from the lancet, and the control member 48 is manually moved out of recess 80 so that the tensioned spring 34 withdraws the lancet and slide 48 through slot portion 76 to the neutral position indicated in FIG. 5. The cap 24 or a new cap may now be placed over the distal end of the housing 12.

Next, the control member 48 is manually moved proximally or downwardly in slot portion 72 compressing coil spring 34 and then over to recess 68 to place the member 48 and holder 16 in a latched retracted or cocked position as shown in FIGS. 1 and 2. The housing 12 may now be hand grasped and the end cap 24 pressed against the skin, such as the skin of the finger, of the person whose blood is to be tested. The control member 48 may now be forced out or the retracted position so that the force of spring 34 and the inertia of the lancet 60 and lancet holder 16 effect piercing of the skin by the needle tip of the lancet and quick removal of the needle from the skin incision to the neutral position as indicated in FIG. 5. The cap 24 may now be removed and the control member 48 moved to the lancet access position as shown in FIG. 6 so that the used lancet may be easily and safely removed from the injector 10 and discarded. At this time, a new lancet may be inserted into the holding member 30 and the control member again moved to the neutral position of FIG. 5 so that the device is again ready to be used to effect skin piercing.

The blood flow caused by the lancet piercing the skin may be collected in a capillary tube or pipette and subjected to clinical testing. For example, at times, glucose testing may be done relatively often in the case of diabetics. Also, such testing may be self-performed such as in the home for monitoring blood glucose.

The lancet injector device 10 effects a very quick incision and withdrawal of the lancet needle so that patient discomfort is minimized. Since the lancet is substantially hidden by the housing, one does not see the lancet point during use and the anxiety of the patient is generally substantially less than where one sees the lancet point. Also, the injector 10 is easy to operate.

The injector 10 requires only one functional spring while operating in a simple and highly effective manner. The spring 34 is shown as a single coil propulsion compression spring which propels the lancet holder 16 for the skin piercing operation. Spring 34 provides the force for piercing the skin as well as swiftly withdrawing the lancet from the incision. The spring 34 is also tensioned when the device is in its lancet access position (FIG. 6) so that its force is also used to quickly withdraw the exposed lancet needle to the neutral position (FIG. 5) when the control member 48 is moved accordingly. Also, spring 34 provides the arcuate biasing force normally urging the slide 48 leftwardly when such bias is employed in the device. The construction of device 10 requires few moving parts and, in general, is simple and economical to make and use.

The housing 12, holder 16 and plug 20 may be economically molded from any suitable plastic, for example, from a copolymer made from acrylonitrile, butadiene, and styrene (ABS), or polypropylene. The cap 24 may also be made from a suitable plastic such as polypropylene. While a snap-on type cap 24 is shown, other cap constructions allowing attachment and removal are possible."

A problem with the lancet injectors of the two above-referenced patents is that the lancet tip must be manually removed from the lancet holder 30 after the lancet has been retracted from the skin of the subject. During this removal process, the lancet tip is exposed and in close proximity to the fingers of the person removing the lancet tip. This increases the possibility that the person removing the lancet may become inadvertently stuck by the lancet tip. In addition to the dangers inherent in puncture wounds, there is the additional danger that the person removing the lancet tip may become infected with a blood borne disease transmitted through the stick from a contaminated lancet tip. These are of course problems to be avoided.

SUMMARY OF THE INVENTION

A lancet injector is provided having a lancet tip that may be automatically removed from the lancet injector after piercing and being retracted from the skin of the subject. The present invention is used in combination with a lancet injector including a generally tubular housing having a patient contacting or distal end and an opposed distal end. The invention also includes, within the housing, a lancet holder having a central bore coaxial with the central axis of the housing and a spring that biases the lancet holder toward the distal end of the housing. The lancet holder frictionally holds the lancet so that the lancet needle is aligned with the central axis and directed toward the distal end of the housing.

An external control member is connected to the holder through a slot in the housing. The control member is constrained to move along the slot because of the contact between the slot and the connection of the holder and control member. The control member moves the holder to a retracted position against the bias of the spring. A separation recess extends from the slot along the housing toward the proximal end of the housing to allow the control member to move proximally in the separation recess. The separation recess has a proximally extending retention recess having means to retain the lancet holder in its most proximal position A pin extends from the proximal end of the housing along the central axis of the housing toward the central bore of the holder. As the holder is moved proximally by movement of the control member through the slot into the separation recess, the pin moves into the central bore of the holder. As the control member is moved into the separation recess, the pin in the central bore of the lancet holder comes into contact with the lancet. The pin stops proximal movement of the lancet during further proximal movement of the control member in the separation recess thereby causing the lancet to be pushed to the edge of frictional contact with the lancet holder. Movement of the control member proximally into the retention recess moves the lancet out of frictional contact with the holder.

Thereafter, the distal end of the lancet injector is directed downward into an appropriate sharps container. The lancet, now free from frictional retaining contact with the lancet holder, falls from the lancet injector into the sharps container.

It is therefore an object of the invention to provide a lancet injector where a used lancet may be removed without requiring manual contact with the lancet.

It is another object of the invention to provide a lancet injector that simply and easily removes the lancet from the lancet injector.

It is a further object of the invention to provide a lancet injector having lancet tips that are automatically removable from the lancet injector without requiring hand contact with the lancet that is relatively simple to manufacture and easy to operate.

These and other objects of the invention will become clear from the description contained herein and more particularly with reference to the following detailed description of the invention with reference to the drawings attached hereto.

BRIEF DESCRIPTION OF THE DRAWINGS

FIG. 13 is an enlarged view of the separation recess and retention recess of the device of FIG. 12 circled in phantom in FIG. 12;

FIG. 14 is cross-sectional view of the control member of the embodiment of FIG. 12;

FIG. 18 is a side elevational view of an alternate embodiment of the invention.

DETAILED DESCRIPTION

Figure 1:
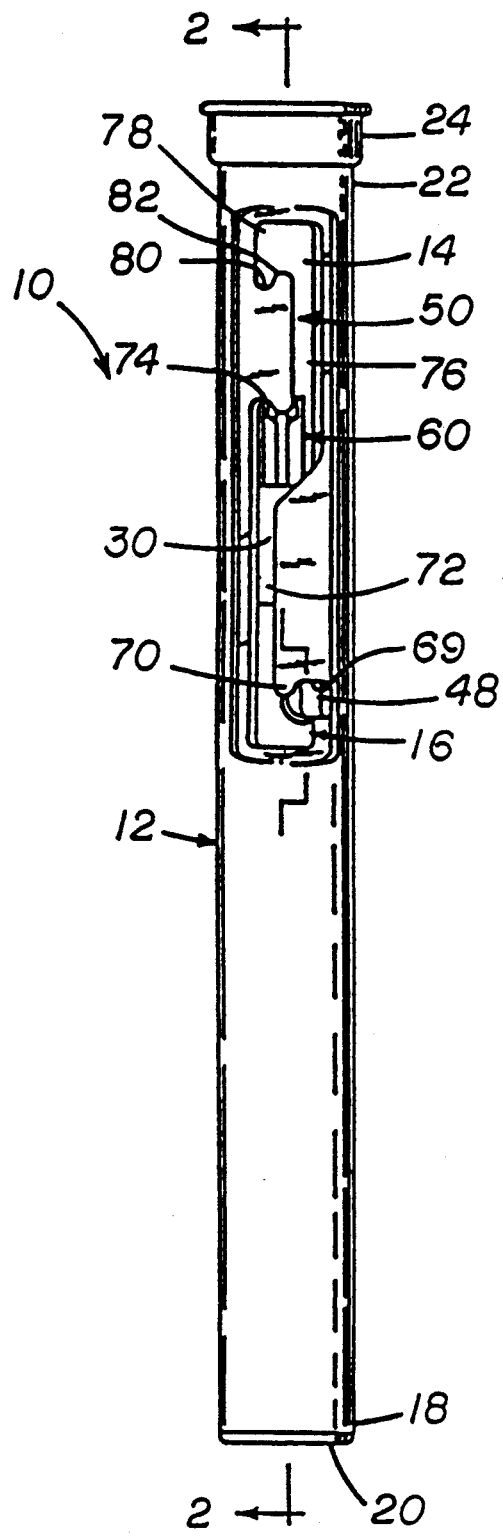
FIG. 1 is a side elevational view of a prior art lancet injector device.
Figure 2:
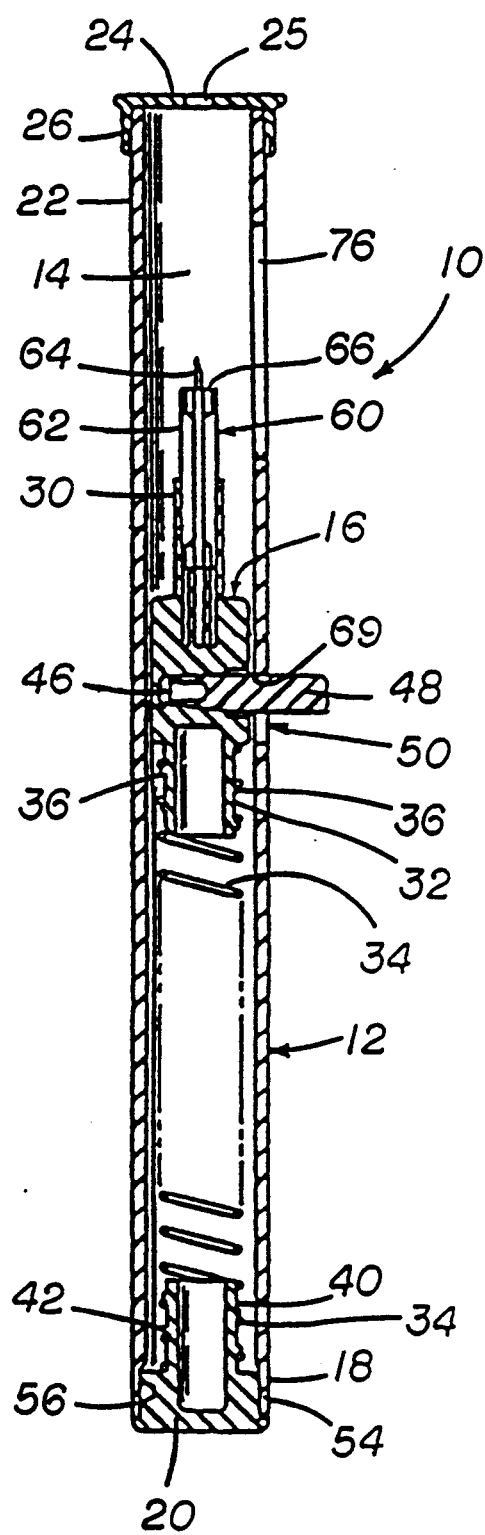
FIG. 2 is a cross-sectional view of the injector device of FIG. 1.
Figure 5:
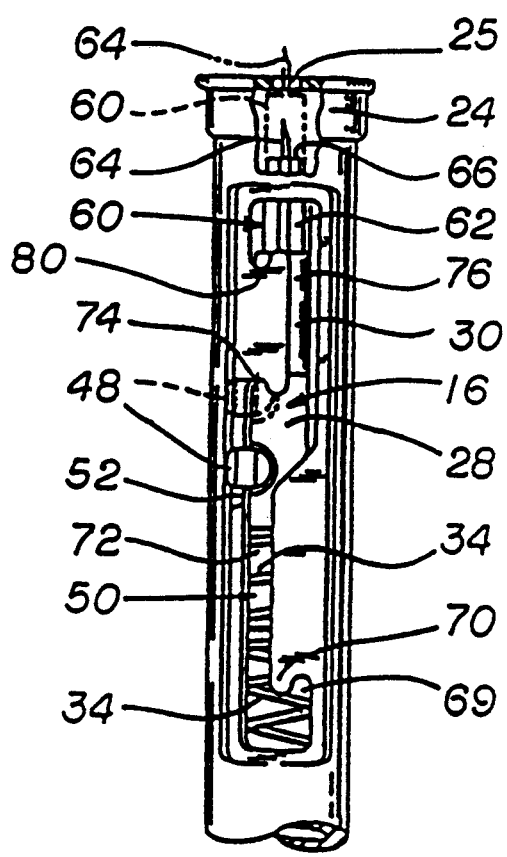
FIG. 5 is a fragmentary side elevational view showing the upper portion of the injector device of FIG. 1 and illustrating the lancet in phantom in its skin piercing position, and the lancet and holder in the neutral position.
Figure 6:
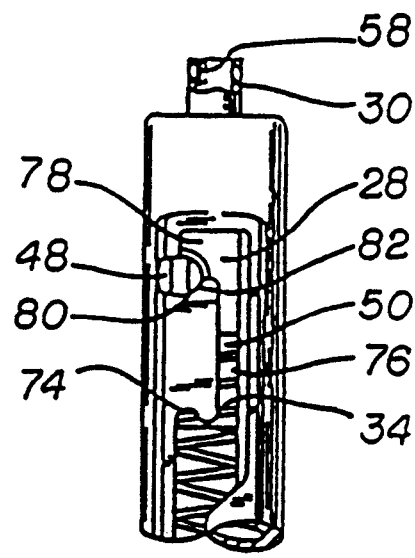
FIG. 6 is a fragmentary side elevational view of the upper portion of the injector device of FIG. 1 showing the lancet holder and in its lancet loading and unloading position with the lancet removed from the device.
Figure 4:
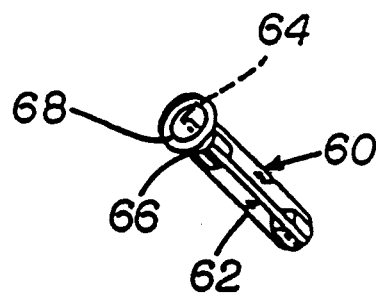
FIG. 4 is a perspective view of the lancet of FIG. 1.
Figure 3:
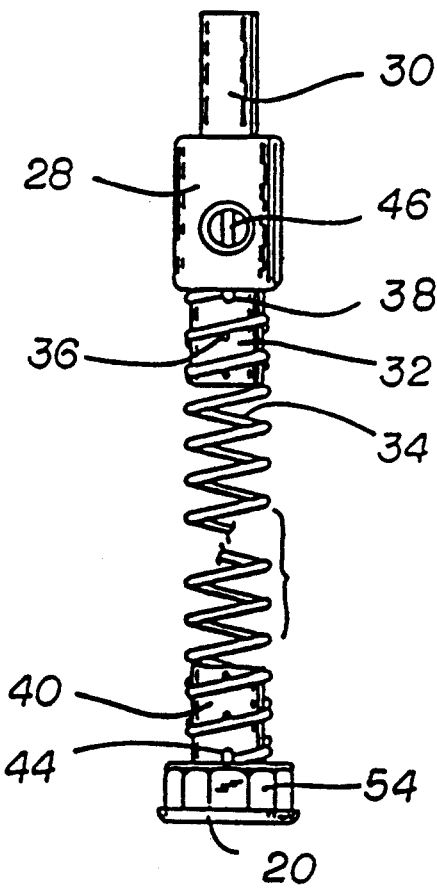
FIG. 3 is a side elevational view of an assembly of parts employed in the injector device of FIG. 1.
Figure 7:
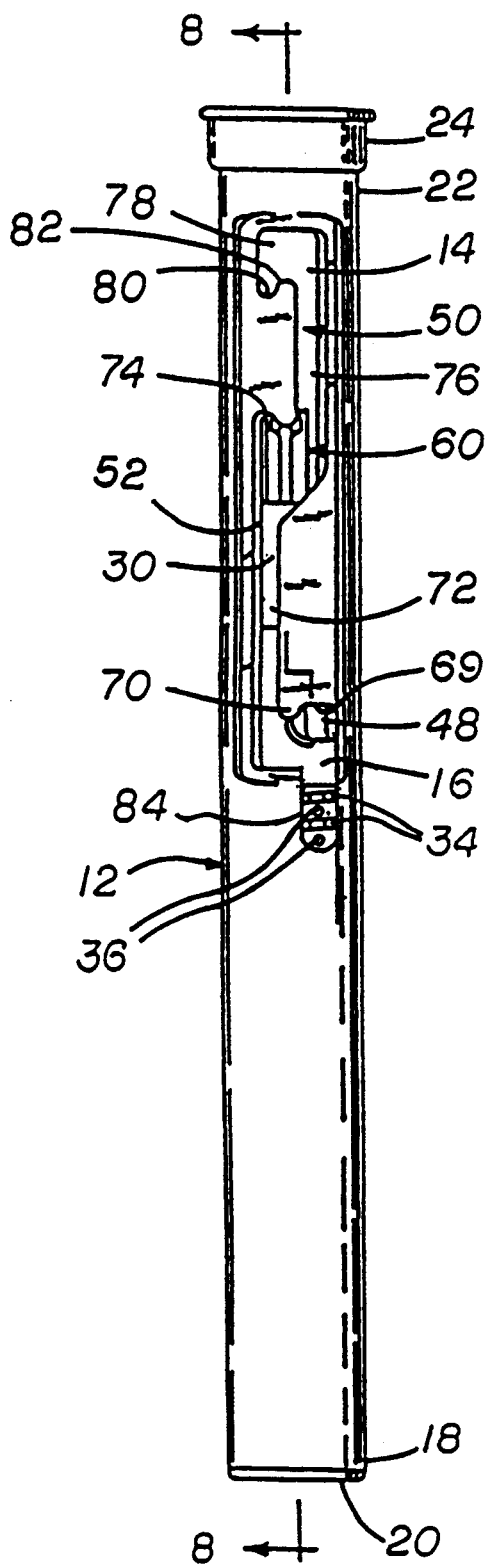
FIG. 7 is a side elevational view of the lancet injector device of FIG. 1 incorporating the present invention.

Referring to the drawings and particularly to FIG. 7, the lancet injector device of FIG. 1 is shown with slot 50 modified by the inclusion of a separation recess 84 extending axially along housing 12 opposite axial recess 69. Separation recess 84 is sufficiently wide to allow control member 48 to be moved into and along it. As control member 48 moves along separation recess 84, lancet holder 16 moves along with it in bore 14 of housing 12. In particular, as control member 48 is moved proximally along separation recess 84, lancet holder 16 is drawn proximally toward end plug 20.

Figure 10:
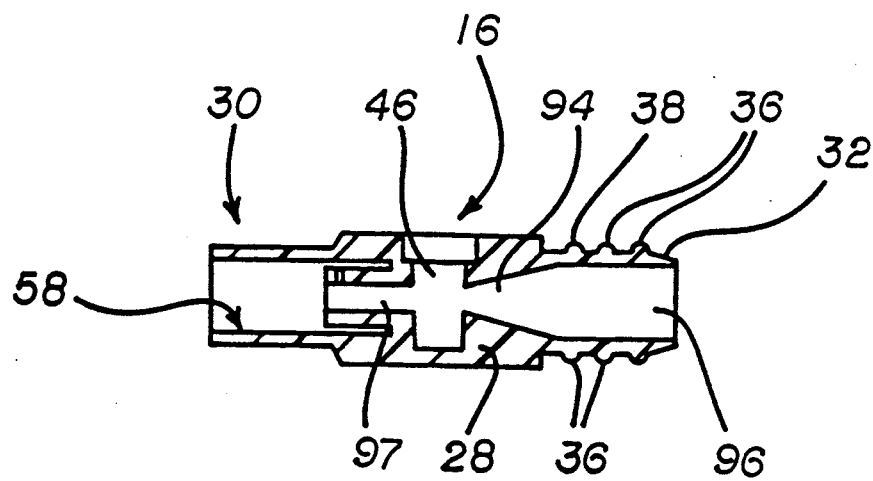
FIG. 10 is a cross-sectional view of the lancet holder of the lancet injector device of FIG. 7.

The lancet injection device of FIG. 1 is also modified in the present invention by placing a central bore 94 through lancet holder 16 as shown in FIG. 10. Central bore 94 extends entirely through lancet holder 16 including extending through slide 28, spring connector 32 and lancet holding member 30. Central bore 94 preferably has an enlarged proximal end 96 within spring connector 32 that tapers to the distal end 97 of central bore 94. Because central bore 94 extends entirely through lancet holder 16, it provides access to the bottom end 67 of lancet 60 through bore 94 when lancet 60 is placed in position in lancet holding member 30.

Figure 8:
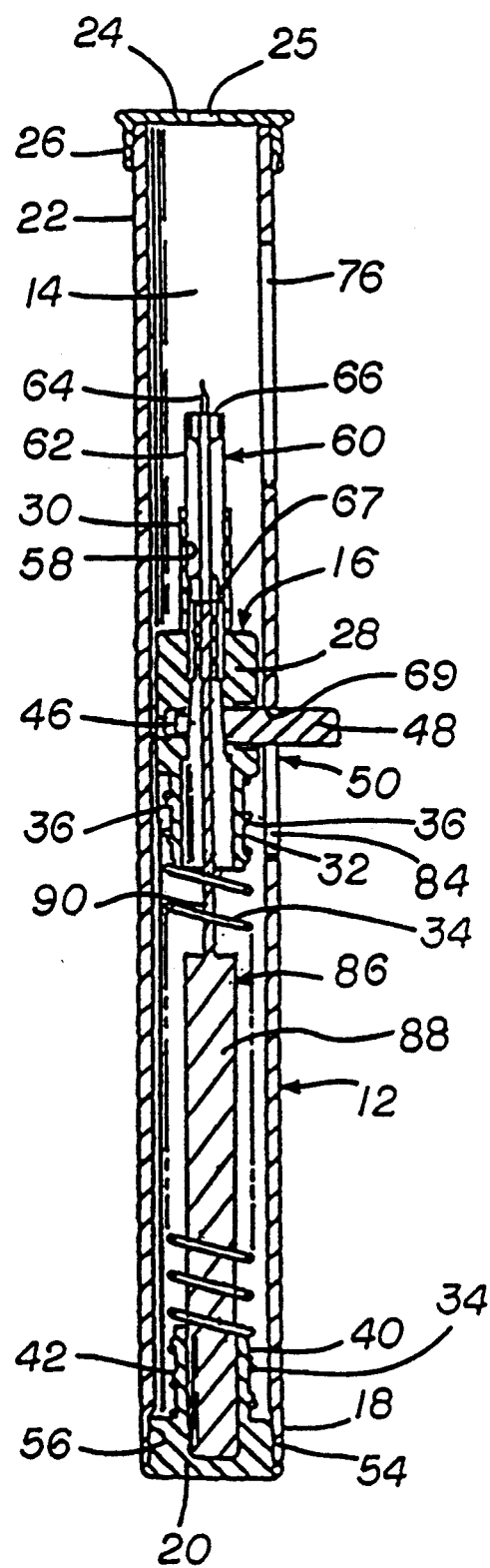
FIG. 8 is a cross-sectional view of the injector device of FIG. 7.
Figure 9A:
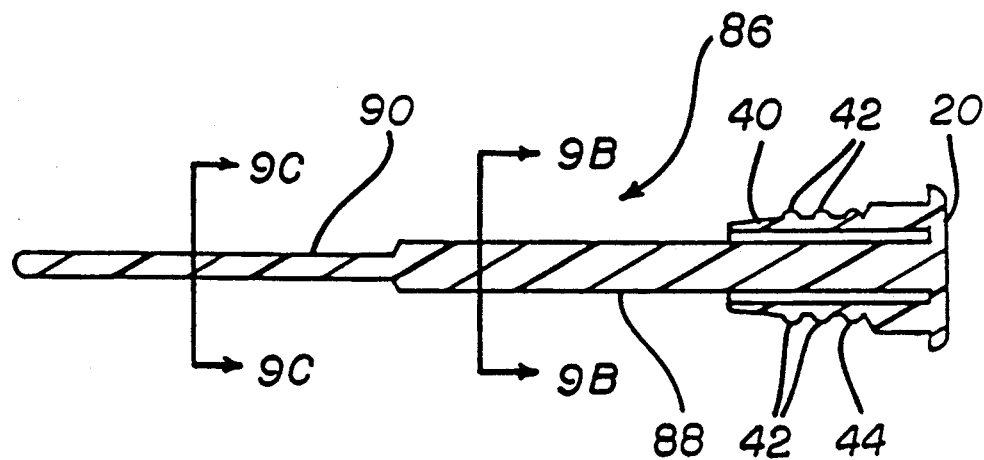
FIG. 9a is a side elevational view of the pin of the injector device of FIG. 7.
Figure 9B:
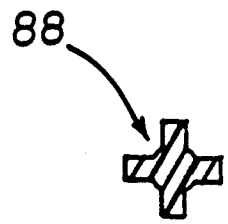
FIG. 9b is a cross-sectional view of the pin of FIG. 9a through line B—B.

A pin 86 (FIG. 9a) is molded in part with end plug 20 at the proximal end 18 of housing 12 within spring connector 40 as shown in FIG. 8. Pin 86 includes an enlarged part 88 and a narrow part 90. Enlarged part 88 is preferably "cross-shaped" in cross-section as shown in FIG. 9b and is of sufficient stiffness and rigidity to support narrow part 90 and to provide a connection between narrow part 90 and spring connector 40. Although enlarged part 88 is preferably "cross-shaped" in cross-section, other cross-sections are possible and within the scope of the invention so long as they perform the functions of supporting and connecting narrow part 90 as described above. An advantage of the "cross-shaped" cross-section is that the amount of material needed to mold enlarged part 88 is reduced as compared to a more solid cross-section.

Figure 9C:
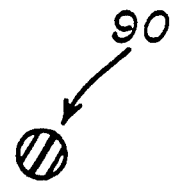
FIG. 9c is a cross-sectional view of the pin of FIG. 9a through line A—A

Narrow part 90 is preferably circular in cross-section as shown in FIG. 9c. This circular shape facilitates the insertion of narrow part 90 through the central bore 94 as will be described hereafter.

As shown in FIG. 8, pin 86 is positioned within and along the central axis of spring 34 and extends from end plug 20 to a point where the most distal end of narrow part 90 just contacts the bottom end 67 of lancet when control member 48 is in the "retracted" position. When lancet holder 16 is moved proximally through housing 12 as control member 48 moves from the "neutral" position to the "retracted" position, narrow part 90 extends into and through the central bore 94.

Figure 11:
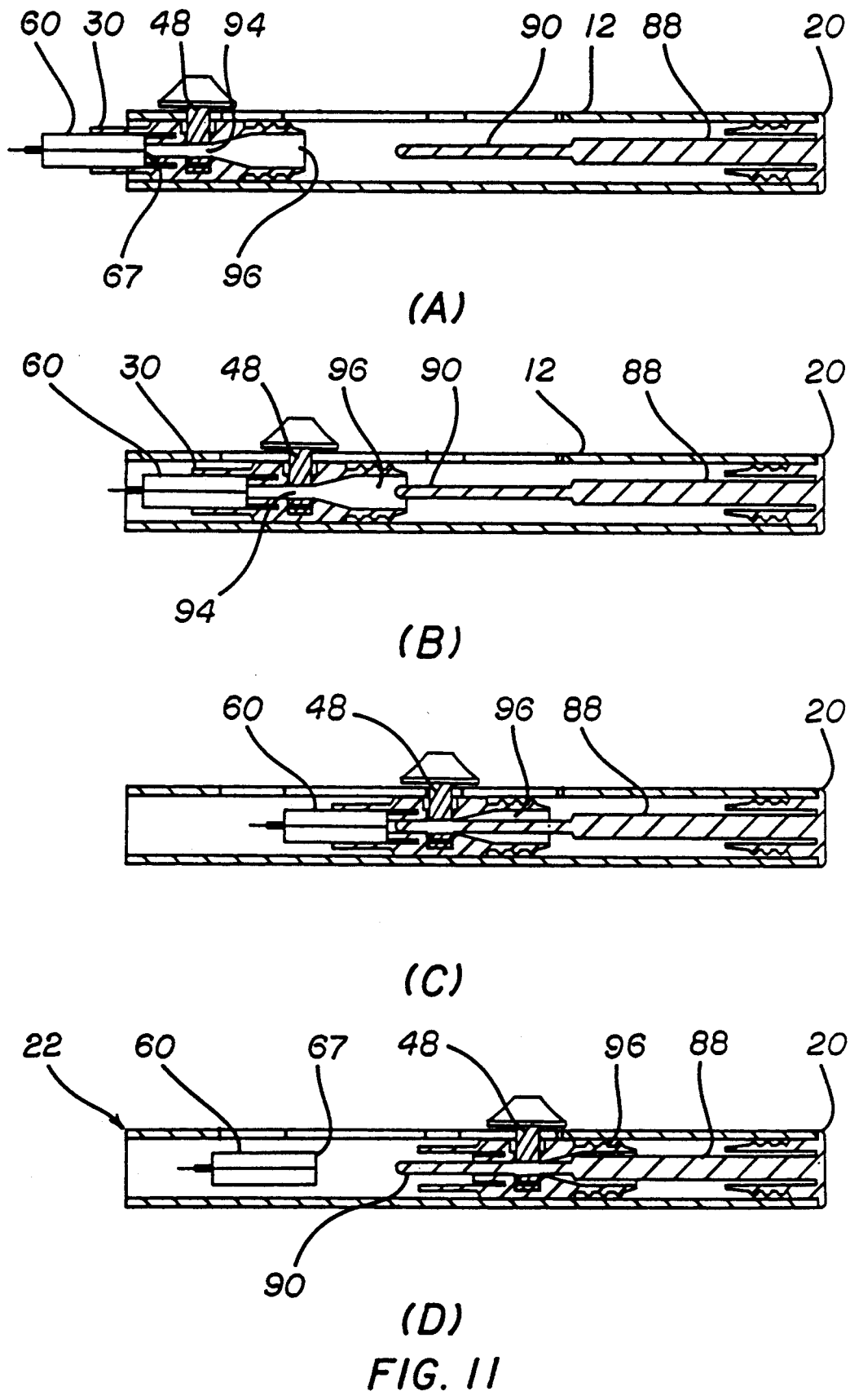
FIG. 11a is a cross-sectional view of the lancet injector device of FIG. 7 in the "load" position.
FIG. 11b is a cross-sectional view of the lancet injector device of FIG. 7 in the "neutral" position.
FIG. 11c is a cross-sectional view of the lancet injector device of FIG. 7 in the "retracted" position.
FIG. 11d is a cross-sectional view of the lancet injector device of FIG. 7 in the "separation position"

FIGS. 11a-d show cross-sectional views of the present invention in operation. In FIG. 11a, control member 48 has been moved forward to the "load" position. A lancet 60 has been placed in position in lancet holding member 30 so that the outer walls of lancet 60 are in frictional contact with inner sidewalls 58 of lancet holding member 30. In the "load" position, pin 86 does not protrude through the central bore 94 of lancet holder 16.

As control member 48 is moved to the "neutral" position, as shown in FIG. 11b, the most proximal end of narrow part 90 of pin 86 extends into the enlarged distal end 96 of lancet holder 16 but does not extend into the narrow distal end 97 of central bore 94 of lancet holding member 30 and consequently does not strike the bottom end 67 of lancet 60.

After lancet needle 64 has punctured skin of the subject as described above and has returned to the "neutral" position shown in FIG. 11b, control member 48 is retracted proximally through slot 50 to the "retracted" position shown in FIG. 11c. In the "retracted" position, spring 34 is slightly compressed providing a bias against lancet holder 16 which pushes control member 48 into contact with axial recess 69. Contact between control member 48 and axial recess 69 holds lancet holder 16 in the "retracted" position. At this time, or previously when control member 48 was in the "neutral" position after having punctured the skin of the subject, the removable cap 24 is removed from the distal end 22 of housing 12. When control member 48 is moved to the "retracted" position as shown in FIG. 11c, the narrow part 90 of pin 86 moves through the enlarged proximal end 96 and through central bore 94 of lancet holder 16 into a position nearly in contact with the bottom end 67 of lancet 60. In this position, any further proximal movement of control member 48 brings the most distal end of narrow part 90 into contact with bottom end 67 of lancet 60.

As shown in FIG. 11d, as control member 48 is moved proximally into separation recess 84, the distal end of narrow part 90 comes into contact with the bottom end 67 of lancet 60. As control member 48 is moved further proximally, contact between the distal end of narrow part 90 and lower end 67 of lancet 60 causes lancet 60 to become separated from its frictional contact with lancet holding member 30. Further, as control member 48 is moved proximally from the "retracted" position shown in FIG. 11c, spring 34 becomes highly compressed therefore strongly biasing control member 48 toward the "retracted" position shown in FIG. 11c. Also, as can be seen in FIG. 11d, when control member 48 is moved to its most proximal position known as the "separation position", the enlarged part 88 of pin 86 extends into the enlarged proximal end 96 of lancet holder 16.

In the "separation position" shown in FIG. 11d, lancet 60 has been removed from frictional contact with lancet holding member 30 so that it is loosely positioned distal to lancet holding member 30. As stated above, in the "separation position", spring 34 provides a strong bias on control member 48 which is countered by the operator of lancet injector 10 holding control member 48 in the "separation position" preferably by finger or thumb contact with control member 48. The bias and counter force on control member 48 is also present on lancet holder 16.

Because of the bias of spring 34 on lancet holder 16, if the operator of lancet injector 10 removes his finger or thumb from control member 48 before lancet 60 has been removed from frictional contact with lancet holder 16 and allowed to fall into an appropriate sharps container, the bias of spring 34 forces control member 48 distally from the "separation position" in separation recess 84 to contact with the axial recess 69 of slot 50. As control member 48 moves from the "separation position" to contact with the axial recess 69, lancet holding member 30 contacts the bottom end 67 of lancet 60 and accelerates it along the bore 14 of housing 12. When control member 48 contacts axial recess 69, lancet holder 16 stops, but lancet 60 continues to move along bore 14 and is ejected out of the distal end 22 of housing 12. This is a problem to be avoided.

Therefore it is desirable to prevent an "ejection" of lancet 60 when the user accidentally removes his finger or thumb from contact with control member 48 as it is moved in separation recess 84. This is done by forming a retention recess 98 extending from separation recess 84 into which the control member 48 must move before lancet 60 is removed from frictional contact with lancet holding member 30. Retention recess 98 retains control member 48 within retention recess 98 so that the housing 12 of the lancet injector 10 may be directed downward into the appropriate sharps container thereby allowing lancet 60 to fall into the sharps container. Any premature release of control member 48 before it is moved and secured in retention recess 98 will cause lancet holder 16 to move distally under the bias of spring 34 but, because lancet 60 is still in frictional contact with lancet holding member 30, lancet 60 will be retained in frictional contact with lancet holding member 30 when control member 48 comes into contact with axial recess 69.

Figure 12:
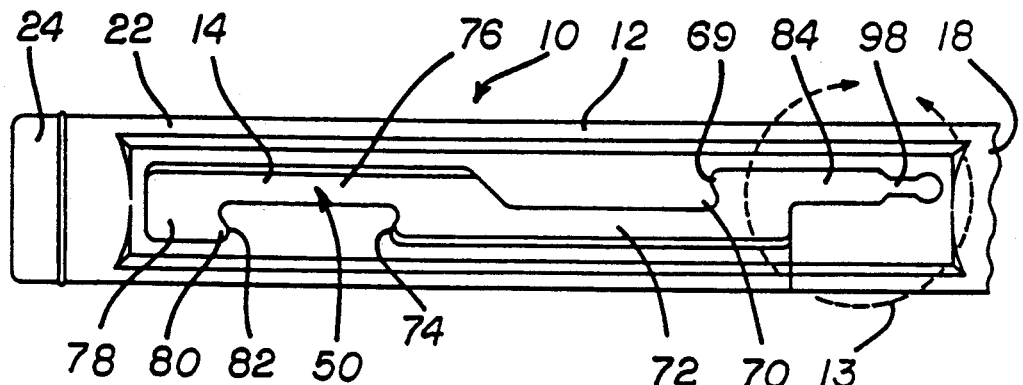
FIG. 12 is a side elevational view of the preferred embodiment of the lancet injector device having a retention recess.

A preferred embodiment for retention recess 98 is shown in FIGS. 12-15. As seen in FIG. 12, separation recess 84 is modified by including a retention recess 98 extending proximally and axially along housing 12 from the most proximal end of separation recess 84. As is shown in more detail in FIG. 13, retention recess 98 includes a narrow bore 100 that opens into an expanded roughly circular shaped proximal stop 102.

In this embodiment, control member 48 is modified in cross-section as shown in FIG. 14 to include an expanded end 104 at the most proximal end of control member 48. The cross-sectional shape of expanded end 104 is approximately the same as the interior shape of proximal stop 102. The transverse width of control member 48 distal to expanded end 104 is approximately the same as the inside diameter of narrow bore 100. Further, at least the part of control member 48 that will move proximally into contact with retention recess 98 should be made of a resilient material for a purpose that will be explained hereafter. The resilient material of control member 48 is preferably the same resilient material as housing 12 as explained above.

Figure 15A:
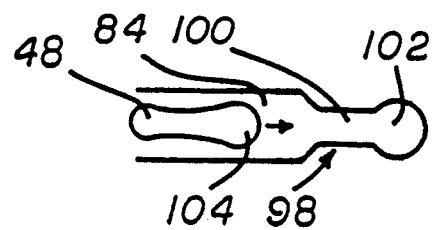
FIG. 15a is a schematic embodiment of the control member of FIG. 14 moving into the retention recess of FIG. 13.
Figure 15B:
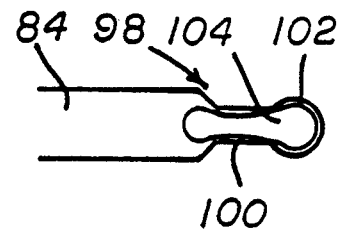
FIG. 15b is a schematic view of the control member of FIG. 14 in position within the retention recess of FIG. 13.

FIG. 15a shows the control member 48 moving proximally from separation recess 84 into retention recess 98. As proximal expanded end 104 moves through narrow bore 100, because the transverse width of expanded end 104 is wider than narrow bore 100, expanded end 104 deforms to pass through narrow bore 100 into proximal stop 102 as shown in FIG. 15b. Because expanded end 104 is no longer compressed within bore 100, it expands to its full non-deformed dimensions that closely correspond to the shape of proximal stop 102.

Spring 34 biases control member 48 distally in retention recess 98 so that expanded end 104 comes into frictional contact with the material of housing 12 narrowing from proximal stop 102 to form narrow bore 100. This frictional contact between expanded end 104 and the entrance to narrow bore 100 retains control member 48 at the proximal end of retention recess 98 despite the bias of spring 34.

When it is desired to release control member 48 so that the bias of spring 34 causes control member 48 to move back into contact with axial recess 69, distal pressure is placed on control member 48. This distal pressure causes expanded end 104 to deform to move into narrow bore 100 thereby allowing control member 48 to pass through bore 100. When control member 48 has passe through bore 100, the bias of spring 34 moves control member 48, and by extension holder 16, proximally until control member 48 contacts axial recess 69.

Although the shape of proximal stop 102 and expanded end 104 have been described as being roughly circular, any other shape may be used so long as the transverse width of expanded end 104 is larger than the width of narrow bore 100.

Figure 16:
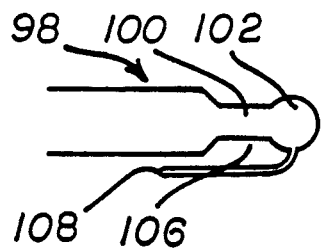
FIG. 16 is a side elevational view of an alternate embodiment of the retention recess of the present invention.

FIG. 16 shows a modification of the embodiment shown in FIGS. 12-15. In FIG. 16, narrow bore 100 is formed by a protrusion 106 pivotally attached to housing 12 at pivot point 108. Protrusion 106 is integrally made with housing 12 and pivot point 108 is preferably a narrow piece of the material of housing 12 so that protrusion 106 flexes with transverse movement of protrusion 106. Transverse pressure on protrusion 106 causes it to move away from retention recess 98.

In this embodiment, as the expanded end 104 of control member 48 moves proximally, contact between expanded end 104 and protrusion 106 causes protrusion 106 to move away from expanded end 104 thereby allowing expanded end 104 to move past protrusion 106. Because of the resilient material at pivot point 108, as stop 104 moves past protrusion 106, protrusion 106 is biased back toward control member 48. Spring 34 biases expanded end 104 into frictional contact with the proximal side of protrusion 106. The frictional contact between stop 104 and protrusion 106 retains control member 48 in position at the proximal end of retention recess 98.

When it is desired to release control member 48 so that the bias of spring 34 causes control member 48 to move back into contact with axial recess 69, distal pressure is placed on control member 48. This distal pressure causes protrusion 106 to move away from expanded end 104 thereby allowing control member 48 to pass through bore 100. When control member 48 has passed through bore 100, the bias of spring 34 moves control member 48, and by extension holder 16, proximally until control member 48 contacts axial recess 69.

Figure 17A:
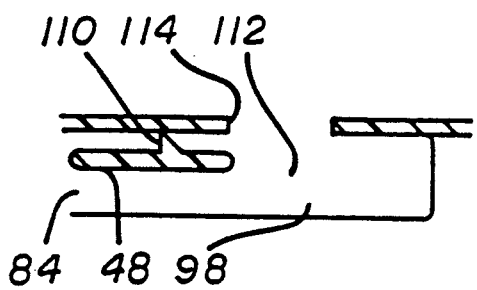
FIG. 17a is a side elevational view of an alternate embodiment of the retention device of the present invention before the device is locked in the retaining position.
Figure 17B:
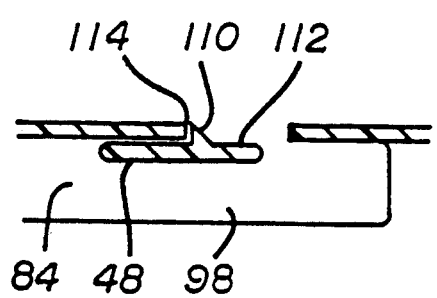
FIG. 17b is a side elevational view of the embodiment of FIG. 17a wherein the control member is locked in position within the retention recess.

A further embodiment of the invention is shown in FIGS. 17a and 17b. In FIG. 17a, control member 48 has a protrusion 110 extending transverse to the elongated axis of control member 48. A slot 112 extends away from retention recess 98 into housing 12 so that a lip 114 is formed on the distal end of slot 112.

In operation, as control member 48 is moved sufficiently proximally into recess 98, protrusion 110 moves past lip 114. At this point, control member 48 can be moved toward slot 112 so that protrusion 110 comes into contact with lip 114. When proximal pressure on control member 48 is removed, the bias of spring 34 will place protrusion 110 into frictional contact with lip 114 thereby retaining control member 48 in position within retention recess 98. When it is desired to allow control member 48 to move back into contact with axial recess 69, control member 48 is moved away from slot 112 so that 110 moves out of contact with lip 114. At this time, spring 34 then moves control member 48 distally.

A further embodiment of the invention is shown in FIG. 18. In this embodiment, a retention protrusion 116 is formed between separation recess 84 and retention recess 98. In the embodiment shown in FIG. 18, retention recess 98 is formed at an angle to separation recess 84 although retention recess 98 may also be formed along a common linear axis with separation recess 84.

Control member 48 is moved past retention protrusion 116 into retention recess 98. There, the bias of spring 34 pushes control member 48 into contact with retention protrusion 116. Frictional contact between control member 48 and retention protrusion 116 holds control member 48 in position within retention recess 98.

When control member 48 is to be moved back into contact with axial recess 69, control member 48 is moved along retention protrusion 116 until it clears retention protrusion 116. At this point, the bias of spring 34 moves control member 48 distally.

The present invention has been described in connection with specific embodiments attached to a particular lancet injector. The foregoing description has been given by means of example only and not is intended to be limiting. Changes and modifications may be made to the description contained herein and still be within the scope of the invention. Further, obvious changes and modifications will occur to those skilled in the art. In addition, alternate embodiments of the invention will occur to those skilled in the art.

We claim:

1. In a lancet injector having a hollow housing with a slot in the housing extending generally longitudinally of the housing, a lancet holder movable within the housing and adapted to hold a lancet, a lancet capable of being held in the lancet holder, a control member connected to the lancet holder and extending through the slot to the exterior of the housing, the control member being movable to a retracted position in the slot, the control member being movable from the retracted position distally to a lancet skin piercing position, the control member being distally movable longitudinally in the slot beyond the skin piercing position to an access position wherein the lancet holder can be loaded with a lancet, an improvement comprising:

the housing further including means for allowing the control member to move proximally beyond the slot in the housing, said means for allowing comprising a separation recess extending generally proximally from the slot in the housing;

means for removing the lancet from the lancet holder when the lancet holder is moved proximally beyond the slot in the housing beyond a predetermined point, said means for removing the lancet form the lancet holder comprising:

a pin rigidly attached to and extending from the proximal end of the housing into the hollow housing along the central axis of the housing; and, wherein the lancet holder has a central bore extending through the lancet holder along the longitudinal axis of the lancet holder, the central bore sized to allow said pin to pass through the lancet holder to contact the proximal end of a lancet when a lancet is positioned in the lancet holder;

means for retaining the control member at the proximal end of said separation recess, said means for retaining comprising a retention recess extending generally proximally from the proximal end of said separation recess, said retention recess having means for retaining the control member within said retention recess, said means for retaining comprising:

said retention recess including a narrow bore that opens into an expanded roughly circular proximal stop;

wherein the control member is modified in cross-section to include an expanded roughly circular end at the most proximal end of the control member, the cross-sectional shape of said expanded end is approximately the same as the interior shape of said proximal stop, the transverse width of the control member distal to said expanded end is approximately the same as the inside diameter of said narrow bore; and, wherein at least the part of the control member that will move proximally into contact with said retention recess should be made of a resilient material.

2. In a lancet injector having a hollow housing with a slot in the housing extending generally longitudinally of the housing, a lancet holder movable within the housing and adapted to hold a lancet, a lancet capable of being held in the lancet holder, a control member connected to the lancet holder and extending through the slot to the exterior of the housing, the control member being movable to a retracted position in the slot, the control member being movable from the retracted position distally to a lancet skin piercing position, the control member being distally movable longitudinally in the slot beyond the skin piercing position to an access position wherein the lancet holder can be loaded with a lancet, an improvement comprising:

the housing further including means for allowing the control member to move proximally beyond the slot in the housing, said means for allowing comprising a separation recess extending generally proximally from the slot in the housing; and, means for removing the lancet from the lancet holder when the lancet holder is moved proximally beyond the slot in the housing beyond a predetermined point, said means for removing the lancet from the lancet holder comprising:

a pin rigidly attached to and extending from the proximal end of the housing into the hollow housing along the central axis of the housing; and, wherein the lancet holder has a central bore extending through the lancet holder along the longitudinal axis of the lancet holder, the central bore sized to allow said pin to pass through the lancet holder to contact the proximal end of a lancet when a lancet is positioned in the lancet holder.

3. A lancet injector comprising:

a hollow housing, said housing having a slot in said housing extending generally longitudinally of said housing;

a lancet holder movable within said housing and adapted to hold a lancet;

a lancet capable of being held in the lancet holder;

a control member connected to said lancet holder and extending through said slot to the exterior of said housing, said control member being movable to a retracted position in said slot, said control member being movable from the retracted position distally to a lancet skin piercing position, said control member being distally movable longitudinally in said slot beyond the lancet skin piercing position to an access position wherein said lancet holder can be loaded with a lancet;

means for allowing the control member to move proximally beyond the slot in the housing; and, means for removing the lancet from the lancet holder when the lancet holder is moved proximally beyond the slot in the housing beyond a predetermined point.

4. The lancet injector of claim 21 wherein said means for removing the lancet from the lancet holder comprises a pin rigidly attached to and extending from the proximal end of the housing into the hollow housing along the central axis of the housing and wherein the lancet holder has a central bore extending through the lancet holder along the longitudinal axis of the lancet holder, the central bore sized to allow said pin to pass through the lancet holder to contact the proximal end of a lancet when a lancet is positioned in the lancet holder.

5. The lancet injector of claim 3 wherein said means for allowing comprises a separation recess extending generally proximally from the slot in the housing.

6. The lancet injector of claim 5 further comprising means for retaining the control member at the proximal end of said separation recess.

7. The lancet injector of claim 6 wherein said means for retaining comprises a retention recess extending generally proximally from the proximal end of said separation recess, said retention recess having means for retaining the control member within said retention recess.

8. The lancet injector of claim 7 wherein said means for retaining comprises:

said retention recess including a narrow bore that opens into an expanded proximal stop; and, wherein the control member is modified in cross-section to include an expanded end at the most proximal end of the control member, the cross-sectional shape of said expanded end is approximately the same as the interior shape of said proximal stop, the transverse width of the control member distal to said expanded end is approximately the same as the inside diameter of said narrow bore.

9. The lancet injector of claim 8 wherein said expanded proximal stop and said expanded end are roughly circular.

10. The lancet injector of claim 8 wherein at least the part of the control member that will move proximally into contact with said retention recess should be made of a resilient material.

11. The lancet injector of claim 10 wherein the resilient material of the control member is preferably the same resilient material as the housing.

12. The lancet injector of claim 3 further comprising means for distally biasing said lancet holder.

13. The lancet injector of claim 12 wherein said means for distally biasing comprises a spring located within said housing and connecting said lancet holder to the proximal end of said housing.

14. In a lancet injector having a hollow housing with a slot in the housing extending generally longitudinally to the housing, a lancet holder movable within the housing and adapted to hold a lancet, a lancet capable of being held in the lancet holder, a control member connected to the lancet holder and extending through the slot to the exterior of the housing, the control member being movable to a retracted position in the slot, the control member being movable from the retracted position distally to a lancet skin piercing position, the control member being distally movable longitudinally in the slot beyond the skin piercing position to an access position wherein the lancet holder can be loaded with a lancet, an improvement comprising:

the housing further including means for allowing the control member to move proximally beyond the slot in the housing; and, means for removing the lancet from the lancet holder when the lancet holder is moved proximally beyond the slot in the housing beyond a predetermined point.

15. The lancet injector of claim 14 wherein said means for removing the lancet from the lancet holder comprises a pin rigidly attached to and extending from the proximal end of the housing into the hollow housing along the central axis of the housing and wherein the lancet holder has a central bore extending through the lancet holder along the longitudinal axis of the lancet holder, the central bore sized to allow said pin to pass through the lancet holder to contact the proximal end of a lancet when a lancet is positioned in the lancet holder.

16. The lancet injector of claim 14 wherein said means for allowing comprises a separation recess extending generally proximally from the slot in the housing.

17. The lancet injector of claim 16 further comprising means for retaining the control member at the proximal end of said separation recess.

18. The lancet injector of claim 17 wherein said means for retaining comprises a retention recess extending generally proximally from the proximal end of said separation recess, said retention recess having means for retaining the control member within said retention recess.

19. The lancet injector of claim 18 wherein said means for retaining comprises:

said retention recess including a narrow bore that opens into an expanded proximal stop; and, wherein the control member is modified in cross-section to include an expanded end at the most proximal end of the control member, the cross-sectional shape of said expanded end is approximately the same as the interior shape of said proximal stop, the transverse width of the control member distal to said expanded end is approximately the same as the inside diameter of said narrow bore.

20. The lancet injector of claim 19 further comprising means for biasing the lancet holder distally; and, wherein the control member has a protrusion extending transverse to the elongated axis of the control member; and, the housing has a retention slot extending away from said retention recess into the housing so that a lip is formed on the distal end of said retention slot;

whereby, as the control member is moved sufficiently proximally into said retention recess, said protrusion moves past said lip thereby allowing the control member to be moved toward said retention slot so that said protrusion comes into contact with said lip so that the bias of said means for biasing places said protrusion into frictional contact with said lip thereby retaining the control member in position within said retention recess.

21. The lancet injector of claim 20 wherein said means for biasing comprises a spring located within the housing and connecting the lancet holder to the proximal end of the housing.

22. The lancet injector of claim 19 wherein said expanded proximal stop and said expanded end are roughly circular.

23. The lancet injector of claim 19 wherein at least the part of the control member that will move proximally into contact with said retention recess should be made of a resilient material.

24. The lancet injector of claim 23 wherein the resilient material of the control member is preferably the same resilient material as the housing.

25. The lancet injector of claim 18 wherein said means for retaining comprises:

the control member being modified in cross-section to include an expanded end at the most proximal end of the control member; and, wherein said retention recess includes a narrow bore, said narrow bore being formed by a protrusion pivotally attached to the housing at a pivot point so that said protrusion flexes with transverse movement of said protrusion whereby transverse pressure on said protrusion by the control member as the control member moves into said narrow bore causes said protrusion to move away from said retention recess.

26. The lancet injector of claim 25 wherein said protrusion is integrally made with the housing and pivot point is preferably a narrow piece of the material of the housing.

27. The lancet injector of claim 18 wherein the housing includes a means for biasing the holder distally to a lancet skin piercing position, and wherein a retention protrusion is formed between said separation recess and said retention recess so that as the control member is moved past said retention protrusion into said retention recess, the bias of said means for biasing pushes the control member into contact with said retention protrusion thereby causing frictional contact between the control member and said retention protrusion that holds the control member in position within said retention recess.

28. The lancet injector of claim 27 wherein said retention recess is formed at an acute angle to said separation recess.

29. The lancet injector of claim 27 wherein said means for biasing comprises a spring located within the housing and connecting the lancet holder to the proximal end of the housing.

30. The lancet injector of claim 14 further comprising means for retaining the control member at the proximal end of said means for allowing.

31. The lancet injector of claim 30 wherein said means for retaining comprises a retention recess extending generally proximally from the proximal end of said means for allowing, said retention recess having means for retaining the control member within said retention recess.

* * * * *